United States Patent [19]

Horwath

[11] Patent Number: 4,568,638

[45] Date of Patent: Feb. 4, 1986

[54] METHOD FOR SCREENING MICROORGANISMS FOR THE PRODUCTION OF GLUCOSE-2-OXIDASE

[75] Inventor: Robert O. Horwath, Westport, Conn.

[73] Assignee: Nabisco Brands, Inc., Parsippany, N.J.

[21] Appl. No.: 495,194

[22] Filed: May 16, 1983

[51] Int. Cl.$^4$ .................. C12Q 1/04; C12Q 1/02; C12R 1/645

[52] U.S. Cl. ........................ 435/34; 435/29; 435/911

[58] Field of Search ............... 435/4, 14, 29, 25, 26, 435/34, 105, 132, 138, 148, 190, 189, 192, 299, 300, 301, 261, 911

[56] References Cited

U.S. PATENT DOCUMENTS

| | | | |
|---|---|---|---|
| 3,981,773 | 9/1976 | Galzy et al. | 435/911 |
| 4,246,347 | 1/1981 | Neidleman et al. | 435/105 |
| 4,321,323 | 3/1982 | Maselli et al. | 435/105 |
| 4,321,324 | 3/1982 | Maselli et al. | 435/105 |
| 4,351,902 | 9/1982 | Neidleman et al. | 435/137 |
| 4,423,149 | 12/1983 | Amon, Jr. et al. | 435/105 |
| 4,440,855 | 4/1984 | Horwath et al. | 435/105 |
| 4,442,207 | 4/1984 | Horwath et al. | 435/105 |
| 4,447,531 | 5/1984 | Horwath et al. | 435/911 |

FOREIGN PATENT DOCUMENTS 0042221 12/1981 European Pat. Off. ............ 435/105

OTHER PUBLICATIONS

Whitaker, J. R. *Principles of Enzymology for the Food Sciences*, Marcel Dekker, Inc., pp. 561–570, 1972.

*Primary Examiner*—Thomas G. Wiseman
*Assistant Examiner*—Jayme A. Huleatt
*Attorney, Agent, or Firm*—Richard Kornutik

[57] ABSTRACT

A process for screening microorganisms to identify those microorganisms capable of the production of glucose-2-oxidase is disclosed. Microorganisms are cultured on a solid medium. Those capable of producing glucose-2-oxidase are identified by reaction of the hydrogen peroxide surrounding each such microorganism with a hydrogen peroxide indicating reagent. The process is particularly useful for the early detection of glucose-2-oxidase activity in slow growing strains of microorganisms such as Basidiomycetes.

15 Claims, No Drawings

METHOD FOR SCREENING MICROORGANISMS FOR THE PRODUCTION OF GLUCOSE-2-OXIDASE

FIELD OF THE INVENTION

This invention relates to the field of microbiology and more particularly to the selection and screening of microorganisms.

BACKGROUND OF THE INVENTION

A variety of approaches has been used to improve the economy of biologically-based industrial processes by "improving" the organism involved. These techniques constitute what may be categorized as strain improvement programs. The efficacy of improving said processes is dependent on the type of organism and the nature of the end-product.

The success of any strain improvement program will be directly affected by the facility with which genetic diversity can be generated in the subject organism, or alternatively the ease with which the genetic diversity already present in nature can be evaluated.

A colony that appears on agar medium following plating out of spores, cells, or small hyphal fragments consists of a population of cells most of which are genetically identical, although some cells may differ due to spontaneous mutation during the growth of the colony or to nuclear heterogeneity in the original propagule.

It was the rare occurrence of spontaneous mutations within existing cultures that provided the major source of strain improvement germplasm in the early years of the fermentation industry. A secondary source of improved strains was nature itself, that is, the isolation from nature of previously unknown strains with improved characteristics.

As a fuller understanding of the biological and chemical basis of genetic change developed, strain improvement programs incorporated this new knowledge into their rationale. For example, induced mutagenesis to generate genetic diversity followed by the subsequent screening, selection and purification of superior strains represents one of the most effective means of improving the yield of a fermentation product. Mutation programs are vital to the fermentation industry in that higher productivities exhibited by the new strains are essential in reducing costs.

It is now appreciated that the choice of a particular mutagen as well as the actual conditions of mutagenesis can play a major role in determining the types and numbers of mutants recovered during a strain improvement program. In general, two experimental approaches have been used to recover new strains resulting from induced mutagenesis experiments; these are: screening and selection.

In a screening system all strains grow with the exception of those killed outright as a result of the mutagenesis treatment; thus each isolate must be examined to identify the desired characteristic. Since tens of millions of isolates must be examined, this approach can be highly labor intensive.

In a selection system, the experimental conditions are chosen so as to establish a growth differential between the rare strains possessing the desired characteristic and all other strains which do not possess said trait. In certain instances the selected strain will not grow under the conditions of the experiment while the non-selected strains will grow. Thus, by removing the growing strains by filtration or other means, the size of the population of cells remaining to be examined is dramatically reduced. Alternatively, conditions may be established such that the selected strain will grow while the non-selected strains are inhibited, here again effectively reducing the population to be examined.

Although induced mutagenesis has been an extremely powerful force in the area of strain improvement, there are some limitations. For example, as more and more mutations are accumulated in a strain as a result of the continuing improvement program, a saturation level is reached. Subjecting such a strain to further selection often results in a loss of productivity due to reversion of existing mutations.

A more fundamental limitation exists in induced-mutation based improvement programs, namely, such programs are based on the assumption that the strains possess the activity to be improved. In other words, the organism must possess, in its genetic repertoire, the information to direct the synthesis of a gene product before any genetically-based improvement program relating to the function of the product may be considered.

A variety of genetic approaches has been developed to reduce these limitations. For example, hybridization techniques allow for genetic recombination to occur among a number of different strains. Hybridization can be achieved by means of sexual reproduction or asexual processes such as somatic cell fusion or heterokaryon formation. The advent of recombinant DNA technology has reduced the limitations on improvement programs even further. The ability to transfer genes between organisms of widely divergent genetic backgrounds has provided the experimenter with a virtually limitless supply of genetic information upon which to improve. This advent of genetic engineering technology has prompted a renewed interest in natural sources of genetic variability, not with a view toward isolating and developing new strains, per se, but rather as a source of as little as a single gene which may be transferred to already established strains.

Regardless of the source of the variant strain, be it either nature, a spontaneous mutation, an induced mutation, or a recombinant resulting from sexual, asexual or genetic engineering processes, methods of screening and selection remain of critical importance, allowing the experimenter to recover the variant strain from among the population of existing strains from which it arose.

In light of the subject invention, one group of organisms of particular interest with regard to strain improvement programs are those useful for the isomerization of glucose to fructose.

Most food grade glucose is provided as an enzymatic hydrolysate of corn starch, i.e., the corn syrup of commerce. Glucose is generally rated at being 60 to 80% as sweet as sucrose and therefore sells at a correspondingly lower price. It has long been known to isomerize glucose to fructose which is even sweeter than sucrose, by employing an enzyme having glucose isomerase activity. Preferably, such an enzyme is one which has been immobilized onto insoluble supports, such as by crosslinking the enzyme with the support matrix or entrapment in a polymer matrix support such as diethylaminoethyl cellulose or porous glass. The isomerization of glucose provides an equilibrium mixture typically containing 42–50% fructose and is referred to as high fructose corn syrup (HFCS).

Recently, it has been proposed to achieve substantially complete conversion of glucose to fructose by first enzymatically converting glucose to glucosone and thereafter chemically reducing the glucosone to fructose. Thus, in accordance with U.S. Pat. No. 4,246,347, at least about ninety-five percent of D-glucose in aqueous solution is enzymatically oxidized to D-glucosone employing an enzyme having glucose-2-oxidase activity, preferably one obtained from *Polyporus obtusus* or *Aspergillus oryzae*, while removing or utilizing co-produced hydrogen peroxide, the D-glucosone being thereafter hydrogenated to D-fructose. As is known in the art, the glucose-2-oxidase obtained from *Polyporus obtusus*, the preferred organism up to the present, is employed in the form of cell-free extract, primarily because only low enzyme activity is obtained when mycelia of this organism are used as the source of the enzyme.

These conversions, D-glucose to D-glucosone and D-glucosone to D-fructose, can be regarded as proceeding in accordance with the following equations:

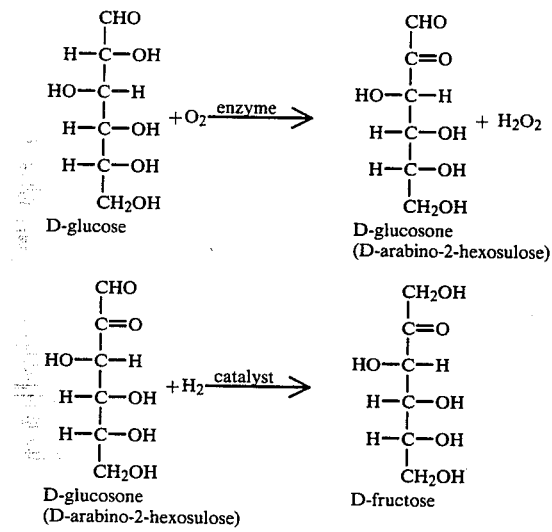

Recently, it has been disclosed in U.S. Pat. Nos. 4,442,207 issued Apr. 10, 1984 and 4,447,531 issued May 8, 1984 that various species of Basidiomycetes produce significant quantities of glucose isomerase and glucose-2-oxidase. These findings, particularly when taken in light of the methods of fructose production as described above, warranted the development of a large scale, efficient screening system for the recovery of glucose-2-oxidase producing strains. It is the principle object of the instant invention to provide such a screening system.

BRIEF DESCRIPTION OF THE INVENTION

This invention relates to a rapid screening method for the detection of increased or decreased production of glucose-2-oxidase by any microorganism.

The invention process for screening microorganisms for the production of glucose-2-oxidase comprises the steps of forming a screening plate comprising a suspension of said microorganisms on a solid or semi-solid medium which promotes the growth of said microorganisms and provides a substrate for the production of hydrogen peroxide by said enzyme; incubating said inoculated medium under conditions that promote the synthesis of glucose-2-oxidase; and identifying in situ those colonies expressing glucose-2-oxidase activity by detecting the presence of hydrogen peroxide by reaction with an analytically indicatable reagent.

The microorganism is plated onto the surface of a solid or semi-solid medium. The medium contains all of the basic nutritional requirements of the particular strain as well as any specific factors which may be required to promote the synthesis of or aid in the detection of the desired enzyme. The medium surrounding each colony is assayed for the presence of the enzyme or enzyme product. Assays particularly useful with regard to the subject invention are those which are non-destructive to the microbial colony. However, toxic reagents may be employed for periods of short exposure in the evaluation of the enzyme activity, when the analytical reaction of said reagent is rapid thus ensuring that a few viable cells are likely to remain in the colony even after treatment with the toxic reagent. Thus, the colony producing the enzyme can be used directly as a source of cells for isolation and further evaluation, eliminating the necessity of "replica plating" each screening plate for the purpose of strain maintenance.

The subject invention is particularly useful in that it provides for early detection of glucose-2-oxidase-producing microorganisms and reduces the number of false positive colonies by eliminating a source of competing enzyme activity (i.e., glucose-1-oxidase).

According to one embodiment of the invention, a soil sample containing microorganisms to be screened is plated onto a culture medium containing sorbose. The sorbose, in addition to serving as a carbon source for the growth of the desired organism, also serves as a substrate for glucose-2-oxidase. As the organism metabolizes the sorbose by means of glucose-2-oxidase, one of the products of said metabolism, hydrogen peroxide, is liberated into the medium. Hydrogen peroxide-producing colonies can then be identified by reaction with appropriate analytically indicatable reagents and $H_2O_2$-producing colonies isolated from the culture plates.

DETAILED DESCRIPTION OF THE INVENTION

One criterion of strain improvement is a change in the activity and/or amount of a particular enzyme produced by an organism. The subject invention exploits this feature to establish a rapid, inexpensive and non-labor intensive method for the in situ screening of glucose-2-oxidase-producing microorganisms. In a preferred embodiment of the invention, a population of microorganisms to be tested is plated onto a solid growth medium. Microorganisms suitable for screening according to the subject invention include: bacteria, actinomycetes, fungi and unicellular algae, although the invention is particularly useful for screening fungi of the Basidiomycete class.

Basidiomycete fungi are relatively slow-growing microorganisms; a period of time from 3–7 days from the initiation of germination to visible colony formation is not uncommon. This protracted developmental period makes the screening and selection of Basidiomycetes from nature particularly difficult. If, for example, a soil sample containing Basidiomycetes and other soil microbes is plated onto a screening medium and incubated for 3–7 days to allow for the development of the Basidiomycete colonies, the plates would be completely overgrown with contaminating, faster growing microbes present in the soil sample.

In light of the fact that Basidiomycete fungi have been shown to produce glucose-2-oxidase and said enzyme is useful in the conversion of glucose to fructose (U.S. Pat. Nos. 4,442,207 and 4,447,531, a method for the large scale, efficient screening of Basidiomycete fungi for the production of glucose-2-oxidase would be clearly useful. However, because of the slow growth displayed by Basidiomycetes, as discussed above, the early detection of enzyme activity in said fungi during the screening procedure is a necessity. The ability to detect enzyme activity in the subject organism early in its developmental history is not only useful in the screening of soil samples (e.g., preventing overgrowth of contaminants), but even when screening pure cultures of Basidiomycetes for strain improvement purposes since the reduction of the 3-7 day development period certainly would be an advantage.

Facilitating the early detection of Basidiomycetes expressing glucose-2-oxidase, it has been discovered that the germinating fungi produce measurable amounts of the desired enzyme. Thus, according to a preferred embodiment of the invention, at least one product of the glucose-2-oxidase reaction is detected in the area surrounding the germinating organism by reaction with a suitable analytically indicatable reagent. The detected reaction product acts as a "chemical microscope" permitting the detection of glucose-2-oxidase-producing cells before such cells multiply to form discrete visible colonies.

In most soil sample to be screened, only the spores of Basidiomycetes are present. By virtue of liberating a reaction product of glucose-2-oxidase activity in the area surrounding the barely visible colonies that develop from said spores, a "metabolic shadow" is cast which may be detected by the appropriate reagents. Thus, by recovering germinating spores from the area indicated by a positive indicator reaction, said germinating spores may be isolated quite early in their developmental history.

In light of the subject invention, the enzymic reaction of interest may be represented as follows:

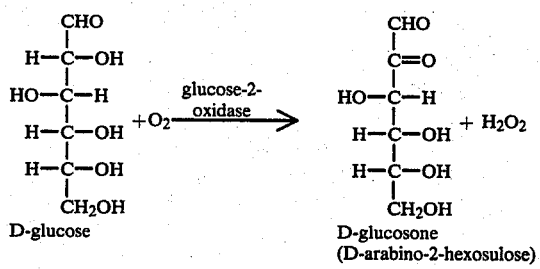

According to the preferred embodiment of the invention, the reaction product, hydrogen peroxide, is detected; although the detection of glucosone is also possible under certain conditions, for example, as described in the cofiled and copending application U.S. patent application, Ser. No. 495,193, filed May 16, 1983.

In order to reduce the number of false positive reactions of the indicator reaction, the subject invention provides for the use of specially selected carbon sources. For example, if glucose, the natural substrate of glucose-2-oxidase, is employed, a variety of false positive reactions will occur due to the metabolism of glucose by other hydrogen peroxide-liberating enzymes, (e.g., glucose-1-oxidase, which catalyzes the oxidation of glucose to glucuronic acid and $H_2O_2$). Because the glucose-2-oxidase can oxidize other carbohydrate substrates not utilized by the competing glucose-1-oxidase, such substrates are employed to reduce false positive reactions. Suitable sole-carbon sources, which reduce false positive reactions include substrates such as sorbose or xylose. Sorbose or xylose may be employed alone or in combination, although due to a lower cost and a more favorable rate of reaction, sorbose is preferred.

Sorbose is converted into 5'-keto-fructose, liberating $H_2O_2$ in the presence of glucose-2-oxidase, whereas sorbose is not an acceptable substrate for glucose-1-oxidase. Furthermore, the presence of sorbose in the screening plates promotes the formation of, but restricts the size of colonial growth of certain microorganisms, thus restricting the spread of said microorganisms. Colony-size limitation is of additional advantage in that a larger number of colonies may be evaluated per plate.

The quantity of sorbose, or xylose, employed usually ranges from about 0.1 to about 5%, preferably from 1% to 3%.

To further illustrate the present invention, the following exemplification is provided.

EXAMPLE 1

This example illustrates the screening of soil samples for glucose-2-oxidase producing microorganisms.

A soil sample is inoculated onto a large screening plate (1.5 liter of medium/plate) and incubated for 48-72 hours at 25° C.

The medium is prepared as follows: All percentages are (w/v).

| | |
|---|---|
| sorbose | 2.0% |
| peptone | 1.0% |
| NaF | 1 mM |
| agar | 2.0% |
| pH | 5.8 |

After the incubation period, the plates are sprayed with the hydrogen peroxide indicator reagent.

The indicator reagent is prepared by mixing 2 parts of ABTS stock solution* with 3 parts peroxidase stock solution.**

*ABTS STOCK SOLUTION ABTS—2.65% (w/v) in water ABTS is the leuco dye, 2,2'azino-di-(3-ethylbenzthiazoline sulfonate).
**PEROXIDASE STOCK SOLUTION 100 units of horseradish peroxidase/ml water (Millipore filtered).

The plates are incubated at 30° C. for up to an additional 24 hours. The formulation of a purple zone indicates the presence of a glucose-2-oxidase producing microorganism.

Alternatively, the ABTS and peroxidase may be combined with agar of the growth medium.

I claim:

1. A process for screening microorganisms to identify those that produce glucose-2-oxidase which comprises the steps of:
   (a) inoculating a suspension of microorganisms on a solid medium which contains sorbose as a sole carbon source for the production of hydrogen peroxide by glucose-2-oxidase produced by said microorganisms;

(b) incubating said inoculated medium under conditions that promote the synthesis of glucose-2-oxidase;

(c) applying a hydrogen peroxide indicating reagent to said medium; and (d) identifying in situ those microorganism colonies expressing glucose-2-oxidase activity by detecting the presence of hydrogen peroxide surrounding said colonies by reaction with said hydrogen peroxide indicating reagent.

2. The process according to claim 1 including the further step of recovering the so-identified microorganisms from said medium.

3. The process according to claim 1 wherein said microorganism is a bacterium, an actinomycete, a fungus or a unicellular alga.

4. The process according to claim 3 wherein said microorganism is a Basidiomycete.

5. The process according to claim 1 wherein said medium comprises from about 0.5% to about 5% w/v sorbose.

6. The process according to claim 5 wherein said medium comprises about 2% w/v sorbose.

7. A process for screening fungal microorganisms to identify those that produce glucose-2-oxidase which comprises the steps of:

(a) inoculating a suspension of fungal microorganisms on a solid medium which contains sorbose as a sole carbon source for the production of hydrogen peroxide by glucose-2-oxidase produced by said fungal microorganisms;

(b) incubating said inoculate medium under conditions that promote the synthesis of glucose-2-oxidase;

(c) applying a hydrogen peroxide indicating reagent to said medium; and (d) identifying in situ those microorganism colonies expressing glucose-2-oxidase activity by detecting the presence of hydrogen peroxide surrounding said colonies by reaction with said hydrogen peroxide indicating reagent.

8. The process according to claim 7 including the further step of recovering the so-identified fungal microorganisms from said medium.

9. The process according to claim 7 wherein said fungal microorganism is a Basidiomycete.

10. The process according to claim 8 wherein said medium comprises from about 0.5% to about 5% w/v sorbose.

11. The process according to claim 10 wherein said medium comprises about 2% w/v sorbose.

12. A process for screening Basidiomycete fungi to identify those that produce glucose-2-oxidase which comprises the steps of:

(a) inonculating a suspension of Basidiomycete fungi on a solid medium which contains sorbose as a sole carbon source for the production of hydrogen peroxide by glucose-2-oxidase produced by said fungi;

(b) incubating said inoculate medium under conditions that promote the synthesis of glucose-2-oxidase;

(c) applying a hydrogen peroxide indicating reagent to said medium; and (d) identifying in situ those fungi colonies expressing glucose-2-oxidase activity by detecting the presence of hydrogen peroxide surrounding said colonies by reaction with said hydrogen peroxide indicating reagent.

13. The process according to claim 12 including the further step of recovering the so-identified Basidiomycete fungi from said medium.

14. The process according to claim 12 wherein said medium comprises from about 0.5% to about 5% w/v sorbose.

15. The process according to claim 14 wherein said medium comprises about 2% w/v sorbose.

* * * * *